(12) United States Patent
Takeuchi et al.

(10) Patent No.: US 6,277,866 B1
(45) Date of Patent: Aug. 21, 2001

(54) 1-BENZYL-4[(5,6-DIMETHOXY-2-FLUORO-1-INDANON)-2-YL]METHYLPIPERIDINE

(75) Inventors: Yoshio Takeuchi; Norio Shibata; Emiko Suzuki, all of Toyama; Yoichi Iimura, Ibaraki; Takashi Kosasa, Ibaraki; Yoshiharu Yamanishi, Ibaraki; Hachiro Sugimoto, Ibaraki, all of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/427,635

(22) Filed: Oct. 27, 1999

(30) Foreign Application Priority Data

Mar. 3, 1999 (JP) .................................................. 11-055754

(51) Int. Cl.$^7$ .................................................. A01N 43/40
(52) U.S. Cl. ........................................... 514/319; 546/205
(58) Field of Search ............................... 514/319; 546/205

(56) References Cited

U.S. PATENT DOCUMENTS 5,100,901 * 3/1992 Sugimoto et al. .................... 514/319

FOREIGN PATENT DOCUMENTS 9-268176 * 10/1997 (JP) .

OTHER PUBLICATIONS

Takeuchi et al., Faculty of Pharmaceutical Sciences, Toyama Medical and Pharmaceutical University, Development of CMIT–F, A New Asymmetric Fluorinating Agent, and the Application to the Chiral Synthesis of Some Fluorinate Bioactive Compounds, P–40, Sugitani 2630, Toyama 930–0194, Japan, p. 291 (Oct. 1998).

Abstracts, 1998 International Symposium on Organic Reactions—Hsinchu, Taiwan (ISOR–1998), pp. 139–140, presented Nov. 14, 1998.

The 22$^{nd}$ Fluorine Conference of Japan, Nov. 20–21, 1998 (with English translation) showing publication date of Oct. 20, 1998.

* cited by examiner

*Primary Examiner*—Ceila Chang
(74) *Attorney, Agent, or Firm*—Birch, Stewart, Kolasch & Birch, LLP

(57) ABSTRACT

The present invention provides a novel compound useful as a medicament, an acetylcholinesterase inhibitor, and an agent for preventing, treating and improving various kinds of senile dementia, Alzheimer-type senile dementia, cerebrovascular dementia or attention deficit hyperactivity disorder, namely, 1-benzyl-4-[(5,6-dimethoxy-2-fluoro-1-indanone)-2-yl]methylpiperidine represented by the following formula:

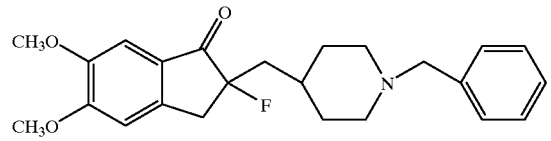

or a pharmaceutically acceptable salt thereof, and a process for producing the same.

4 Claims, No Drawings

1-BENZYL-4[(5,6-DIMETHOXY-2-FLUORO-1-INDANON)-2-YL]METHYLPIPERIDINE

FIELD OF THE INVENTION

The present invention relates to a novel compound useful as a medicament, specifically as an acetylcholinesterase inhibitor, more specifically as an agent for preventing, treating and improving various kinds of senile dementia, cerebrovascular dementia or attention deficit hyperactivity disorder (ADHD), and further specifically as an agent for preventing, treating and improving Alzheimer-type senile dementia, and a process for producing the same.

PRIOR ART

With a rapidly increasing population of the older generation, it is desired to establish a method of treating senile dementia such as Alzheimer-type senile dementia etc., cerebrovascular dementia and attention deficit hyperactivity disorder.

Development of treating agents for these diseases has been studied from various points of view, and in a prominent point of view, development of acetylcholine precursors and acetylcholinesterase inhibitors is proposed because these diseases are accompanied by a reduction in cholinergic functions in the brain, and actually, such compounds are clinically applied. Typical acetylcholinesterase inhibitors include donepezil hydrochloride (1-benzyl-4-[(5,6-dimethoxy-1-indanon)-2-yl]methylpiperidine hydrochloride), rivastigmine (N-ethyl-N-methyl 3-[1-(dimethylamino)ethyl]phenyl carbamate), metrifonate (dimethyl 2,2,2-trichloro-1-hydroxyethyl)phosphate), tacrine hydrochloride (1,2,3,4-tetrahydro-9-acridinamine), galanthamine hydrobromide, neostigmine, physostigmine etc.

However, among these medicaments, it is only donepezil hydrochloride that was confirmed to have a pharmaceutical effect on the diseases in actual clinical application and further observed to have satisfactory usefulness from the viewpoint of side effects and frequency of administration, and the other medicaments have some drawbacks such as poor effect, their undesirable side effects, necessity for frequent administration every day, and limited use in an injection because of their inapplicability to oral administration, so there is no or little choice but to choose donepezil hydrochloride at present.

As described above, donepezil hydrochloride is a superior medicament, but it is needless to say that the presence of acetylcholinesterase inhibitors having more superior effects would be more preferable for a wider choice of medicaments in clinical application.

DISCLOSURE OF THE INVENTION

Under these circumstances, the present inventors have extensively studied various compounds for a long period of time to develop medicaments having more superior effects and higher safety.

As a result, they have found that 1-benzyl-4-[(5,6-dimethoxy-2-fluoro-1-indanon)-2-yl]methylpiperidine or a pharmaceutically acceptable salt thereof can achieve the above object, and completed the present invention.

Accordingly, the object of the present invention is to provide a novel compound useful as a medicament, specifically as an acetylcholinesterase inhibitor, more specifically as an agent for preventing, treating and improving various kinds of senile dementia, cerebrovascular dementia and attention deficit hyperactivity disorder, and further specifically as an agent for preventing, treating and improving Alzheimer-type senile dementia, and a process for producing the same.

The present invention also provides a method of preventing, treating and improving diseases, which is based on the inhibition of acetylcholinesterase and comprises the step of administering the pharmaceutically effective amount of 1-benzyl-4-[(5,6-dimethoxy-2-fluoro-1-indanon)-2-yl]methylpiperidine or a pharmaceutically acceptable salt thereof to a patient, and a method of preventing, treating and improving various kinds of senile dementia, cerebrovascular dementia or attention deficit hyperactivity disorder, which comprises the step of administering the pharmaceutically effective amount of 1-benzyl-4-[(5,6-dimethoxy-2-fluoro-1-indanon)-2-yl]methylpiperidine or a pharmaceutically acceptable salt thereof to a patient.

1-Benzyl-4-[(5,6-dimethoxy-2-fluoro-1-indanon)-2-yl]methylpiperidine according to the present invention (referred to hereinafter as "the compound of the present invention") is represented by the following formula:

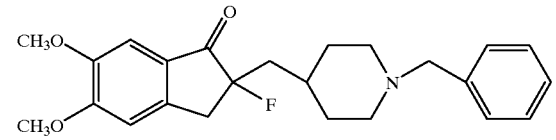

The compound of the present invention has an asymmetric carbon atom in the molecule so there occur 2 kinds of optically active substances and racemates, and the compound of the present invention includes, but is not limited to, such compounds. Further, these compounds may be present in the form of not only anhydrides but also hydrates which are not limited.

The pharmaceutically acceptable salt in the present invention are not particularly limited insofar as it is an addition salt formed with the compound of the present invention, and specifically includes e.g. inorganic acid salts such as hydrochloride, hydrobromide, sulfate, nitrate and phosphate, organic acid salts such as oxalate, maleate and fumarate, and sulfonates such as methane sulfonate, benzene sulfonate and toluene sulfonate. Among these salts, hydrochloride and oxalate are more preferable.

Hereinafter, the conventional process for producing the compound of the present invention is described in detail, but other processes can also be used for production.

(1) Fluorination of 1-benzyl-4-[(5,6-dimethoxy-1-indanon)-2-yl]methylpiperidine

For example, the compound of the present invention can be obtained by fluorinating 1-benzyl-4-[(5,6-dimethoxy-1-indanon)-2-yl]methylpiperidine produced according to Examples 3 and 4 of JP-A 64-79151 (EP-A1 296560).

In this case, a preferable result is observed generally when the starting compound is reacted first with a base and then with a fluorinating agent.

As the base used here, a strong base is prefereble, and specific examples include, but are not limited to, lithium bis(trimethylsilyl) amide, n-butyl lithium, lithium diisopropylamide, sodium amide, sodium hydride, sodium methoxide, sodium ethoxide, potassium t-butoxide, sodium hydroxide and potassium hydroxide etc.

Specific examples of the fluorinating agent include N-fluorobenzensulfonimide (NFSI, CAS Registration No: 133745-75-2), 3-cyclohexyl-2-fluoro-2,3-dihydro-3- methyl-1,1-dioxide-1,2-benzisothiazole (CMIT-F, CAS Reg. No: 186806-24-6, 196106-79-3), 2-fluoro-3,3-dimethyl-2,3-dihydro-1,2-benzisothiazole-1,1-dioxide (CAS Reg. No: 124170-23-6), diethylaminosulfur trifluoride (DAST, CAS Reg. No: 38078-09-0), N,N-diethyl-1,1,2,3,3,3 -hexafluoropropylamine (Ishikawa reagent), hydrogen fluoride, tetraalkyl ammonium fluoride, potassium fluoride, cesium fluoride, hydrogen fluoride-pyridine (Olah reagent) etc. Among these agents, N-fluorobenzenesulfonimide and 3-cyclohexyl-2-fluoro-2,3-dihydro-3-methyl-1,1-dioxide-1,2-benzisothiazole are more preferable.

The solvent used here is not limited insofar as it is inert to the above-mentioned strong bases and fluorinating agents, and specific examples include tetrahydrofuran (THF), 1,2-dimethoxyethane (DME, ethylene glycol dimethyl ether), ethyl ether, isopropyl ether, butyl ether, 1,4-dioxane, 1,3-dioxolane, benzene, toluene, xylene, cyclohexane, n-hexane, n-pentane, n-octane, petroleum ether etc. These may be used alone or as a mixture thereof.

If the optically active substance of the present invention are required, these can be obtained in any one of the following methods:

(1) An optically active fluorinating agent is used.
(2) The racemates are optically resolved.

Hereinafter, Examples are given below to describe the present invention more in detail, however it is needless to say that they are not intended to limit the process for producing the compound of the present invention.

EXAMPLES

Example 1
Synthesis of 1-benzyl-4-[5,6-dimethoxy- 2-fluoro-1-indanon)-2-yl]methylpiperidine hydrochloride

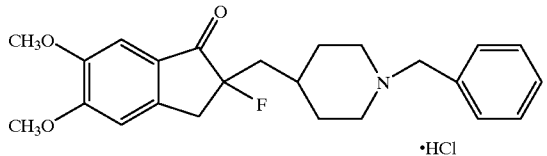

·HCl

The following reaction was conducted in a nitrogen atmosphere.

0.20 g (0.53 mmol) of 1-benzyl-4-[(5,6-dimethoxy-1-indanon)-2-yl]methylpiperidine was dissolved in 10 ml tetrahydrofuran (THF) and cooled to −78° C., and then 0.63 ml (0.63 mmol) of 1.0 M lithium bis(trimethylsilyl)amide/THF solution was poured thereinto. The temperature of the mixture was raised from −78° C. to −20° C. over 45 minutes and then cooled again to −78° C., and a solution of N-fluorobenzenesulfonimide (0.25 g, 0.79 mmol) in THF (2 ml) was poured thereinto. The temperature of the mixture was gradually raised from −78° C. to room temperature. After stirring for 4 hours, a saturated aqueous solution of ammonium chloride (30 ml) was added thereto and the mixture was extracted with 30 ml of ethyl acetate. The organic layer was washed with 30 ml aqueous saturated sodium chloride solution, dried (MgSO$_4$) and evaporated. The resulting residue was purified by silica gel column chromatography (NH-silica gel; methylene chloride/methanol system), whereby the free compound (0.16 g, yield; 76%) of the title compound was obtained as a pale yellow oil.

Free compound;
$^1$H-NMR(270 MHz, C$_6$D$_6$); δ (ppm) 1.35–1.70 (6H,m), 1.84 (2H,m), 2.14 (1H,m), 2.79 (2H,m), 2.86 (1H,dd,J=13.5 Hz,J=17 Hz), 3.03 (1H,dd,J=17Hz,J=22 Hz), 3.21 (3H,s), 3.27 (3H,s), 3.33 (2H,s), 6.20 (1H,s), 7.11–7.23 (4H,m), 7.36 (2H,d,J=7.1 Hz).

This product was converted in a usual manner into hydrochloride and recrystallized from ethanol/isopropyl ether to give the title compound as pale yellow crystals. Hydrochloride;

M.p.: 170 to 172° C.
$^1$H-NMR(400 MHz,CDCl$_3$); δ (ppm) 1.73–2.24 (7H,m), 2.60–2.77 (2H,m), 3.15–3.37 (2H,m), 3.39–3.52 (2H,m), 3.90 (3H,s), 3.98 (3H,s), 4.16 (2H,d,J=4.4 Hz), 6.82 (1H,s), 7.14 (1H,s), 7.40–7.50 (3H,m), 7.58–7.65 (2H,m), 12.10 (1H,bs).

ESI-MS: m/z=398 (M+H$^+$).

Finally, Pharmacological Experiment is given below to show the usefulness of the compound of the present invention as a medicament.

Inhibitory action on acetylcholinesterase in vitro
1) Method

Using a rat brain homogenate as a source of acetylcholinesterase, its esterase activity was measured in accordance with the method of Ellman et al[1]. Acetylthiocholine as the substrate, sample and DTNB (5,5'-dithiobis (2-nitrobenzoic acid)) were added to the homogenate and incubated, whereby the produced thiocholine was reacted with DTNB and the resulting yellow product was measured for the change of absorbance at 412 nm to determine the acetylcholinesterase activity.

[1]: Ellman. G. L., Courtney, K. D., Andres, V. and Featherstone, R. M., (1961), Biochem. Pharmacol., 7, 88–95.

The inhibitory activity of each test compound on acetylcholinesterase was determined in terms of 50% inhibitory concentration (IC$_{50}$).

2) Test compounds
Each of the following compounds was used after dissolved in physiological saline.
  1: The compound of the present invention (hydrochloride);
  2: Donepezil hydrochloride.

3) Results
The experimental results are shown below.

| Compound | IC$_{50}$ (nM) |
| --- | --- |
| 1 | 1.3 |
| 2 | 6.7 |

The superior effect of the compound of the present invention is evident from the above results.

What is claimed is:

1. A method of treating diseases, which is based on the inhibition of acetylcholinesterase and comprises the step of administering the pharmaceutically effective amount of 1-benzyl-4-[(5,6-dimethoxy-2-fluoro-1-indanon)-2-yl] methylpiperidine or a pharmaceutically acceptable salt thereof to a patient.

2. A method of treating various kinds of senile dementia, cerebrovascular dementia or attention deficit hyperactivity disorder, which comprises the step of administering the pharmaceutically effective amount of 1-benzyl-4-[(5,6-dimethoxy-2-fluoro-1-indanon)-2-yl]methylpiperidine or a pharmaceutically acceptable salt thereof to a patient.

3. The method as claimed in claim 2, wherein the senile dementia is Alzheimer-type senile dementia.

4. A process for producing 1-benzyl-4-[(5,6-dimethoxy-2-fluoro-1-indanon)-2-yl]methylpiperidine or a pharmaceutically acceptable salt thereof, which comprises the steps of fluorinating 1-benzyl-4-[(5,6-dimethoxy-1-indanon)-2-yl]methylpiperidine by reacting it with a fluorinating agent selected from the group consisting of N-fluorobenzenesulfonimide and 2-fluoro-3,3-dimethyl-2,3-dihydro-1,2-benzisothiazole-1,1-dioxide;

converting the product as necessary into a salt.

* * * * *